United States Patent
Peng et al.

(10) Patent No.: US 11,209,196 B2
(45) Date of Patent: Dec. 28, 2021

(54) HFO-1234ZE, HFO-1225ZC AND HFO-1234YF COMPOSITIONS AND PROCESSES FOR PRODUCING AND USING THE COMPOSITIONS

(71) Applicant: THE CHEMOURS COMPANY FC, LLC, Wilmington, DE (US)

(72) Inventors: Sheng Peng, Hockessin, DE (US); Mario Joseph Nappa, Leesburg, FL (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 17/193,021

(22) Filed: Mar. 5, 2021

(65) Prior Publication Data

US 2021/0262704 A1    Aug. 26, 2021

Related U.S. Application Data

(63) Continuation-in-part of application No. 17/270,654, filed on Feb. 23, 2021, and a continuation of application No. PCT/US2020/029690, filed on Apr. 24, 2020, which is a continuation-in-part of application No. PCT/US2019/057999, filed as application No. PCT/US2019/057999 on Oct. 25, 2019.

(60) Provisional application No. 62/750,991, filed on Oct. 26, 2018.

(51) Int. Cl.
  *F25B 13/00*   (2006.01)
  *C07C 17/357*  (2006.01)
  *C07C 21/18*   (2006.01)

(52) U.S. Cl.
  CPC .......... *F25B 13/00* (2013.01); *C07C 17/357* (2013.01); *C07C 21/18* (2013.01)

(58) Field of Classification Search
  CPC ....... F25B 13/00; C07C 17/357; C07C 21/18; C09K 5/045; C09K 2205/126
  See application file for complete search history.

(56) References Cited

U.S. PATENT DOCUMENTS

| | | | |
|---|---|---|---|
| 3,413,363 A | 11/1968 | Pindzola | |
| 6,034,289 A | 3/2000 | Christoph et al. | |
| 7,423,188 B2 | 9/2008 | Miller et al. | |
| 7,663,007 B2 | 2/2010 | Rao et al. | |
| 7,862,742 B2 | 1/2011 | Minor et al. | |
| 7,981,312 B2* | 7/2011 | Nappa | C07C 17/25 252/67 |
| 7,985,884 B2 | 7/2011 | Nappa et al. | |
| 8,067,650 B2* | 11/2011 | Wang | C07C 17/38 570/236 |
| 8,148,317 B2* | 4/2012 | Singh | B01F 17/0085 |
| 8,444,874 B2 | 5/2013 | Singh et al. | |
| 8,911,640 B2 | 12/2014 | Nappa et al. | |
| 9,302,962 B2 | 4/2016 | Peng et al. | |
| 9,410,105 B2* | 8/2016 | DeSantis | C10M 141/10 |
| 9,783,720 B2 | 10/2017 | Kontomaris | |
| 9,902,888 B2* | 2/2018 | Leck | B60H 1/3228 |
| 2015/0252281 A1* | 9/2015 | Saito | C09K 5/04 252/68 |
| 2018/0002506 A1* | 1/2018 | Nappa | C09K 3/30 |

FOREIGN PATENT DOCUMENTS

| | | |
|---|---|---|
| EP | 0 486 333 B1 | 12/1994 |
| EP | 3 109 302 A1 | 12/2016 |
| WO | 2013/011291 A1 | 1/2013 |
| WO | 2014/117014 A2 | 7/2014 |
| WO | 2016/132111 A1 | 8/2016 |
| WO | 2020/086928 A1 | 4/2020 |

OTHER PUBLICATIONS

PCT International Search Report and Written Opinion for Application No. PCT/US2019/057999 dated Jan. 21, 2020.
PCT International Search Report and Written Opinion for Application No. PCT/US2020/029690 dated Jul. 9, 2020.
Standard Test Method for Concentration Limits of Flammability of Chemicals (Vapors and Gases), ASTM E681-09, 2015.
Lubricants in Refrigerant Systems, 1990 ASHRAE Handbook, Refrigeration Systems and Applications, Chapter 8, pp. 8.1-8.21, Atlanta, GA.
Shubkin, Ronald L., Editor, Synthetic Lubricants and High Performance Functional Fluids, 1993, Chapter 2, Esters, pp. 43-65 and Chapter 4, Polyalkylene Glycols, pp. 101-123, Marcel Dekker, Inc., New York, NY.
Saunders and Frisch, Polyurethanes Chemistry and Technology, 1962, pp. 193-201 and 219-223, vols. I and II, John Wiley and Sons, New York, NY.

\* cited by examiner

*Primary Examiner* — Filip Zec

(57) ABSTRACT

A fluoropropene composition comprising Z-1,3,3,3-tetrafluoropropene, E-1,3,3,3-tetrafluoropropene, 1,1,3,3,3-pentafluoropropene, 2,3,3,3-tetrafluoropropene, and optionally 1,1,1,3,3-pentafluoropropane wherein the 2,3,3,3-tetrafluoropropene being present in an amount of 0.00001 to 1.0%. A method of producing the fluoropropene, methods for using the fluoropropene and the composition formed are also disclosed.

20 Claims, No Drawings

HFO-1234ZE, HFO-1225ZC AND HFO-1234YF COMPOSITIONS AND PROCESSES FOR PRODUCING AND USING THE COMPOSITIONS

This application is a Continuation of International Application No. PCT/US2020/029690 filed on Apr. 24, 2020 and also is a Continuation-in-Part of U.S. application Ser. No. 17/270,654 filed on Feb. 23, 2021 which is a 371 of International Application No. PCT/US2019/057999 filed Oct. 25, 2019 that claims the benefit of Provisional Application No. 62/750,991 filed Oct. 26, 2018. International Application No. PCT/US2020/029690 is a continuation-in-part of International of PCT Application No. PCT/US2019/057999, filed on Oct. 25, 2019. The disclosures of Application Nos. PCT/US2019/057999, PCT/US2020/029690, Ser. No. 17/270,654, and 62/750,991 are hereby incorporated by reference.

FIELD OF THE INVENTION

The present invention relates to tetrafluoropropene compositions and methods for making and using the compositions and, in particular, to a method for producing and using a product comprising 1,3,3,3-tetrafluoropropene (HFO-1234ze), 1,1,3,3,3-pentafluoropropene (HFO-1225zc), and 2,3,3,3-tetrafluoropropene (HFO-1234yf) prepared from 1,1,1,3,3-pentafluoropropane (HFC-245fa).

BACKGROUND OF THE INVENTION

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefin compositions are believed to meet both goals. Thus, there is also a need for economical manufacturing processes that provide these compositions.

HFO-1234ze ($CF_3CH=CHF$) and HFO-1234yf ($CF_3CF=CH_2$), both having zero ozone depletion and low global warming potential, have been identified as potential refrigerants. U.S. Pat. No. 7,862,742 discloses compositions comprising HFO-1234ze and HFO-1234yf. U.S. Pat. No. 9,302,962 discloses methods for making HFO-1234ze. The disclosures of U.S. Pat. Nos. 7,862,742 and 9,302,962 are hereby incorporated by reference in their entirety.

Catalytic dehydrofluorination of HFC-245fa in general produces a mixture of both the E-isomer as well as the Z-isomer of HFC-1234ze. Depending on the particular catalyst chosen, the amount of the Z-isomer can vary between 15% to 23%. Dehydrofluorination in the liquid phase using aqueous solutions of caustic or other strong bases also produces mixture of both isomers. Although the ratio of the two isomers can be shifted somewhat by temperature, about 13% to about 15% of the Z-isomer is typically formed. As the E-isomer is the most useful for refrigeration applications, after separation of the E-isomer from the Z-isomer, the Z-isomer is typically either isomerized to the E-isomer in a separate step or converted back to 245fa through addition of hydrogen fluoride. Both alternatives require additional steps which add cost.

There is a need in this art for a process that can produce compositions of HFO-1234ze and HFO-1234yf that minimizes or eliminates the need for purification or separation steps for removing excess quantities of HFO-1234yf. In particular, there is a need in this art for an economical process that produces compositions comprising HFO-1234ze, HFO-1225zc and HFO-1234yf wherein the amount of HFO-1225zc and HFO-1234yf are each greater than zero and less than about 1 mole percent and wherein the total amount of HFO-1225zc and HFO-1234yf is less than about 1 mole percent.

BRIEF DESCRIPTION OF THE INVENTION

Described is a fluoropropene composition comprising Z-1,3,3,3-tetrafluoropropene, E-1,3,3,3-tetrafluoropropene, 1,1,3,3,3-pentafluoropropene, 2,3,3,3-tetrafluoropropene, and optionally 1,1,1,3,3-pentafluoropropane. The 2,3,3,3-tetrafluoropropene being present in an amount of 0.00001 to 1.0 mol %, the being present in an amount greater than 0 to 1.0 mole %, and the total amount of 1,1,3,3,3,-pentafluoropropene and 2,3,3,3-tetrafluoropropene is greater than 0 and less than 1.0 mol %

In addition, the present disclosure includes a method of producing a mixture of a fluoropropene of formula $CF_3CH=CHF$ and a fluoropropene of formula $CF_3CF=CH_2$, comprising contacting a mixture of 1,1,1,3,3-pentafluoropropane and Z-,1,3,3,3-tetrafluoropropene in the gas phase with a catalyst comprising at least one catalyst selected from the group consisting of fluorinated Cr2O3 or Cr/Ni on fluorinated alumina, in the presence of an oxygen containing gas, to form a mixture comprising Z-1,3,3,3-tetrafluoropropane, E-1,3,3,3,-tetrafluoropropene, 1,1,3,3,3-pentafluoropropene, 2,3,3,3-tetrafluoropropene, and optionally unreacted 1,1,1,3,3-pentafluoropropane. One embodiment the inventive method produces a useful composition without the need for purification or separation steps including steps for removing excess quantities of 2,3,3,3-tetrafluoropropene (HFO-1234yf) or 1,1,3,3,3-pentafluoropropene.

Further still, the present disclosure includes fluoropropene compositions formed from the method of contacting a mixture of 1,1,1,3,3-pentafluoropropane and Z-,1,3,3,3-tetrafluoropropene in the gas phase with a catalyst comprising at least one catalyst selected from the group consisting of fluorinated Cr2O3 or Cr/Ni on fluorinated alumina, optionally in the presence of an oxygen containing gas.

In one embodiment, the inventive process produces a composition comprising HFO-1234ze(E), HFO-1225zc and HFO-1234yf and the composition is useful as a refrigerant. In another embodiment, the composition comprises HFO-1225zc and a near azeotropic composition comprising HFO-1234ze(E) and HFO-1234yf. In a further embodiment, the composition comprises a three component near azeotropic composition comprising HFO-1234ze(E), HFO-1234yf and HFO-1225zc.

One embodiment relates to any combination of the foregoing wherein the 2,3,3,3-tetrafluoropropene is present in an amount of 0.01 to 1.0 mol %.

One embodiment relates to any combination of the foregoing wherein the 2,3,3,3-tetrafluoropropene is present in an amount of 0.1 to 0.9 mol %.

One embodiment relates to any combination of the foregoing wherein the 2,3,3,3-tetrafluoropropene is present in an amount of 0.2 to 0.4 mol %.

One embodiment relates to any combination of the foregoing wherein the 2,3,3,3-tetrafluoropropene is present in an amount of 0.3 to 0.4 mol %.

One embodiment relates to any combination of the foregoing wherein the fluoropropene composition additionally optionally comprises one or more of R-143a, R-152a, TFP (trifluoropropyne), R-1233xf, R-1233zd(E), R-1233zd(Z), R236fa, and at least one HFO-1234 isomer including at least one of HFO-1234zc, HFO-1234yc and HFO-1234ye.

One embodiment relates to any combination of the foregoing wherein the sum total of the amounts of R-143a, R-152a, TFP, R-1233xf, R-1233zd(E), and R-1233zd(Z) is between 0.001 mole percent and 2 mole percent, based on the total fluoropropene composition.

One embodiment relates to any combination of the foregoing wherein the fluoropropene composition includes R-1233zd(E) in an amount of 0.7 mole percent to 1.15 mole percent, based on the total fluoropropene composition.

One embodiment relates to any combination of the foregoing wherein the fluoropropene composition includes R-1233zd(Z) in an amount of 0.05 mole percent to 0.25 mole percent, based on the total fluoropropene composition.

One embodiment relates to any combination of the foregoing wherein the fluoropropene composition includes R-143a in an amount of 0.05 mole percent to 0.25 mole percent, based on the total fluoropropene composition.

One embodiment relates to any combination of the foregoing wherein the fluoropropene composition optionally comprises one or more of 1224yd, 1224zc, 1326mxz, 113, 32, 23, trifluoropropyne, 356mff, 1326mxz, HFC-245fa and HFC-245cb.

One embodiment relates to any combination of the foregoing wherein the sum total of the amounts 1224yd, 1224zc, 1326mxz, 113, 32, 23, trifluoropropyne, 356mff, 1326mxz, HFC-245fa and HFC-245cb is between 0.001 mole percent and 2 mole percent, based on the total fluoropropene composition.

One embodiment relates to any combination of the foregoing wherein the composition is near azeotropic.

Another embodiment of the invention relates to a method of producing a mixture of a fluoropropene of formula $CF_3CH=CHF$ and a fluoropropene of formula $CF_3CF=CH_2$, comprising:
  contacting a mixture of 1,1,1,3,3-pentafluoropropane and Z-1,3,3,3-tetrafluoropropene in the gas phase with a catalyst comprising at least one catalyst selected from the group consisting of fluorinated $Cr_2O_3$ or Cr/Ni on fluorinated alumina, in the presence of an oxygen containing gas, to form a mixture comprising Z-1,3,3,3-tetrafluoropropene, E-1,3,3,3,-tetrafluoropropene, 2,3,3,3-tetrafluoropropene, hydrogen fluoride, and optionally unreacted 1,1,1,3,3-pentafluoropropane
wherein the mixture includes 0.00001% to 1.00% 2,3,3,3-tetrafluoropropene.

One embodiment of the invention relates to any combination of the foregoing wherein said mixture of 1,1,1,3,3-pentafluoropropane and Z-1,3,3,3-tetrafluoropropene comprises at least 7% by weight Z-1,3,3,3-tetrafluoropropene.

One embodiment of the invention relates to any combination of the foregoing wherein said mixture of 1,1,1,3,3-pentafluoropropane and Z-1,3,3,3-tetrafluoropropene comprises at least 10% by weight Z-1,3,3,3-tetrafluoropropene.

One embodiment of the invention relates to any combination of the foregoing wherein at least 94% by weight of the 1,1,1,3,3-pentafluoropropane is converted to E-isomer of 1,3,3,3-tetrafloropropene.

One embodiment of the invention relates to any combination of the foregoing wherein at least 98% by weight of the 1,1,1,3,3-pentafluoropropane is converted to E-isomer of 1,3,3,3-tetrafloropropene.

One embodiment of the invention relates to any combination of the foregoing and further comprising recovering Z-1,3,3,3-tetrafluoropropene, or a mixture of Z-1,3,3,3-tetrafluoropropene and 1,1,1,3,3-pentafluoropropane, and recycling Z-1,3,3,3-tetrafluoropropene, or a mixture of Z-1,3,3,3-tetrafluoropropene and 1,1,1,3,3-pentafluoropropane back to step (a).

One embodiment of the invention relates to any combination of the foregoing wherein said hydrogen fluoride produced in step (a) is separated and recovered.

One embodiment of the invention relates to any combination of the foregoing wherein said oxygen containing gas is oxygen, or air.

One embodiment of the invention relates to any combination of the foregoing wherein the mixture includes 0.1 to 0.5 mol % 2,3,3,3-tetrafluoropropene.

One embodiment of the invention relates to any combination of the foregoing wherein the mixture includes 0.2 to 0.4 mol % 2,3,3,3-tetrafluoropropene.

One embodiment of the invention relates to any combination of the foregoing wherein the mixture includes 0.3 to 0.4 mol % 2,3,3,3-tetrafluoropropene.

Another embodiment of the invention relates to any combination of the foregoing methods and to a fluoropropene composition produced by these methods.

A further embodiment of the invention relates to any combination of the foregoing embodiments and comprising a refrigerant composition comprising Z-1,3,3,3-tetrafluoropropene, E-1,3,3,3,-tetrafluoropropene, 1,1,3,3,3-pentafluoropropane, and 2,3,3,3-tetrafluoropropene and at least one member selected from the following groups:
  (a) comprising one or more of R-143a, R-152a, TFP, R-1233xf, R-1233zd(E), R-1233zd(Z) 1224yd, 1224zc, 1326mxz, 113, 32, 23, trifluoropropyne, 356mff, 1326mxz, HFC-245fa, HFC-245cb 1234zc, 1234yc, 1234ye, 134a, 1225ye (Z and E), 114, 124, and 236fa,
  (b) comprising one or more of R-143a, R-152a, TFP, R-1233xf, R-1233zd(E), R-1233zd(Z), 1224yd, 1224zc, 1326mxz, 113, 32, 23, trifluoropropyne, 356mff, 1326mxz, HFC-245fa and HFC-245cb,
  (c) comprising one or more of HFC-1234ye, HFC-1243zf, HFC-32, HFC-125, HFC-134, HFC-134a, HFC-143a, HFC-152a, HFC-161, HFC-227ea, HFC-236ea, HFC-236fa, HFC-245fa, HFC-365mfc, R1336mzz(E), propane, n-butane, isobutane, 2-methylbutane, n-pentane, cyclopentane, dimethylether, $CF_3SCF_3$, $CO_2$, and $CF_3I$;
  (d) combinations thereof.

One embodiment of the invention relates to a process for transferring heat, comprising:
  providing an article;
  contacting the article with a heat transfer media;
wherein the heat transfer media comprises the fluoropropene composition of any combination of the foregoing embodiments and including a near azeotropic composition produced by the inventive method.

One embodiment of the invention relates to a process for treating a surface, comprising:
providing a surface;
contacting the surface with a treatment composition;
wherein the surface includes a treatable material deposited thereon; and wherein the treatment composition comprises the fluoropropene composition of any combination of the foregoing embodiments.

One embodiment of the invention relates to any combination of the foregoing wherein the treatment composition substantially dissolves the treatable material.

One embodiment of the invention relates to a process for forming a composition comprising:
providing a solute; contacting the solute with a solvent; wherein the solvent comprises the fluoropropene composition of any of the foregoing embodiments.

Another embodiment of the invention relates to a refrigeration system, comprising:
an evaporator; a condenser;
a compressor; an expansion device;
and a heat transfer media;
wherein the heat transfer media comprises the fluoropropene composition of any combination of the foregoing embodiments and including a near azeotropic composition produced by the inventive method.

The foregoing general description and the following detailed description are exemplary and explanatory only and are not restrictive of the invention, as defined in the appended claims. The various embodiments of the invention can be used alone or in combinations with each other. Other features and advantages of the present invention will be apparent from the following more detailed description of the preferred embodiment, which illustrate, by way of example, the principles of the invention.

DETAILED DESCRIPTION OF THE INVENTION

Described is a method of producing a mixture of a fluoropropene of formula $CF_3CH=CHF$, a fluoropropene of formula $CF_2=CHCF_3$ and a fluoropropene of formula $CF_3CF=CH_2$, comprising contacting a mixture of 1,1,1,3,3-pentafluoropropane and Z-,1,3,3,3-tetrafluoropropene in the gas phase with a catalyst comprising at least one catalyst selected from the group consisting of fluorinated $Cr_2O_3$ or Cr/Ni on fluoride alumina, optionally in the presence of an oxygen containing gas, to form a mixture comprising Z-1,3,3,3-tetrafluoropropene, E-1,3,3,3,-tetrafluoropropene, 1,1,3,3,3-pentafluoropropene, 2,3,3,3-tetrafluoropropene, and, optionally, unreacted 1,1,1,3,3-pentafluoropropane. Without wishing to be bound by any theory or explanation, a higher contact temperature and/or increased length of catalyst contact time can cause formation of an increased amount of 1,1,3,3,3-pentafluoropropene.

Certain dehydrofluorination reactions are well known in the art. The dehydrofluorination of HFC-245fa has been particularly studied. Both gas phase and liquid phases processes are known. 1,3,3,3-tetrafluoropropene (HFO-1234ze) exists as both a Z-isomer and an E-isomer about the double bond. Both gas phase and liquid phase processes are known to produce a mixture of both the Z- and E-isomers, with the E-isomer predominating. The selectivity for the production of the Z-isomer can vary from about 10% to about 23%, depending on the temperature, and choice of catalyst. The boiling point of the E-isomer at 1 atm is about −19° C., while the boiling point of the Z-isomer is about 9° C. For many uses, the E-isomer is preferred. So as to minimize yield losses in the form of the generally unwanted Z-isomer, it becomes necessary to either add an isomerization step to isomerize the Z-isomer to the E-isomer or add a fluorination step to convert HFO-1234ze(Z) back to HFC-245fa.

The dehydrofluorination reaction according to embodiments of the present disclosure may result in compositions of HFO-1234ze(E), HFO-1225zc and HFO-1234yf that minimizes or eliminates the need for purification or separation steps for removing excess quantities of HFO-1234yf or HFO-1225zc. In some cases, the composition may be azeotropic or near azeotropic or include an azeotropic or near azeotropic composition. By azeotropic compositions it is meant a constant-boiling mixture of two or more substances that behave as a single substance. One manner to characterize an azeotropic composition is that the vapor produced by partial evaporation or distillation of a liquid has the same composition as the liquid from which it is evaporated or distilled (i.e., the mixture distills/refluxes without compositional change). Constant-boiling compositions are characterized as azeotropic because they exhibit either a maximum or minimum boiling point, as compared with that of the non-azeotropic mixture of the same compounds. An azeotropic composition will not fractionate within a refrigeration or air conditioning system during operation. Additionally, an azeotropic composition will not fractionate upon leakage from a refrigeration or air conditioning system. In the situation where one component of a mixture is flammable, fractionation during leakage could lead to a flammable composition either within the system or outside of the system.

By a near-azeotropic composition it is meant to refer to a substantially constant boiling liquid admixture of two or more compounds that behave essentially as a single substance. One manner to characterize a near-azeotropic composition is that the vapor produced by partial evaporation or distillation of a liquid has substantially the same composition as the liquid from which it was evaporated or distilled, that is, the admixture distills/refluxes without substantially compositional change. Another manner to characterize a near-azeotropic composition is that the bubble point vapor pressure and the dew point pressure of the composition at a particular temperature are substantially the same. In particular, a composition of the invention is near-azeotropic if, after 50 weight percent (50%) of the composition is removed, such as by evaporation or boiling off, the difference in vapor pressure, between the original composition and the composition remaining after 50 weight percent of the original composition has been removed, is less than about 10 percent (10%).

In accordance with one embodiment of the instant invention, the inventive compositions have a flammability rating of A2L as determined by ASHRAE Standard 34 and ASTM E681-09.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Certain, dehydrofluorinations are known in the art, and are preferably conducted in the vapor phase. The dehydrofluorination reaction may be conducted in any suitable reaction vessel or reactor, but it should preferably be constructed from materials which are resistant to the corrosive effects of hydrogen fluoride, such as nickel and its alloys, including Hastelloy, Monel, and Inconel, or vessels lined with fluoropolymers. These may be a single tube, or multiple tubes packed with a dehydrofluorination catalyst.

Useful catalysts for the process include chromium-based catalysts such as fluorinated chromium oxide, which catalyst may either be unsupported, or supported on a support such as activated carbon, graphite, fluoride graphite, or alumina fluoride. The chromium catalyst may either be used alone, or in the presence of a co-catalyst selected from nickel, cobalt, manganese or zinc salt. In one embodiment, a chromium catalyst is high surface area chromium oxide, or chromium/nickel on alumina fluoride ($Cr/Ni/AlF_3$), the preparation of which is reported in European Patent EP486,333. In another embodiment, the catalyst is fluorinated Guignet's green catalyst. Additional suitable catalysts include, but are not limited to, JM 62-2 (chrome catalyst available from Johnson Matthey), LV(chrome catalyst available from Chemours), JM-62-3 (chrome catalyst available from Johnson Matthey), and Newport Chrome (chrome catalyst available from Chemours). The chromium catalysts are preferably activated before use, typically by a procedure whereby the catalyst is heated to from 350° C. to 400° C. under a flow of nitrogen for a period of time, after which the catalyst is heated under a flow of HF and nitrogen or air for an additional period of time.

In one embodiment, the Guignet's Green of the fluoride-activated Guignet's Green catalyst used in the present invention is made by reacting (fusing) boric acid with alkali metal dichromate at 500° C. to 800° C., followed by hydrolysis of the reaction product, whereby said Guignet's Green contains boron, alkali metal, and water of hydration. The usual alkali metal dichromates are the Na and/or K dichromates. The reaction is typically followed by the steps of cooling the reaction product in air, crushing this solid to produce a powder, followed by hydrolysis, filtering, drying, milling and screening. The Guignet's Green is bluish green, but is known primarily as a green pigment, whereby the pigment is commonly referred to as Guignet's Green. When used as a catalyst, it is also referred to as Guignet's Green as disclosed in U.S. Pat. No. 3,413,363. In U.S. Pat. No. 6,034,289, $Cr_2O_3$ catalysts are disclosed as preferably being in the alpha form, and Guignet's Green is also disclosed as a commercially available green pigment having the composition: $Cr_2O_3$ 79-83%, $H_2O$ 16-18%, $B_2O_5$ 1.5 to 2.7% (sentence bridging cols. 2 and 3) that can be converted to the alpha form (col. 3, l. 3). U.S. Pat. No. 7,985,884 acknowledges the presence of alkali metal in the Guignet's Green in the composition of Guignet's Green disclosed in Example 1: 54.5% Cr, 1.43% B, 3,400 ppm Na, and 120 ppm K. The disclosure of the foregoing patents and patent applications is hereby incorporated by reference.

The physical shape of the catalyst is not critical and may, for example, include pellets, extrudates, powders, or granules. The fluoride activation of the catalyst is preferably carried out on the final shape of the catalyst.

In one embodiment, the instant invention relates to feeding a mixture of HFC-245fa and at least about 10% by weight of the Z-isomer of HFO-1234ze to a dehydrofluorination reactor in the presence of an oxygen containing gas in order to suppress the formation of additional Z-isomer so that the HFC-245fa converted by dehydrofluorination produces substantially only E-HFO-1234ze, HFO-1225zc and HFO-1234yf. Feeding less than about 10% will result in some suppression of the formation of additional Z-1234ze. Feeding greater than about 10% by weight of Z-1234ze simply results in the presence of additional material which must be separated and recycled. The amount of Z-1234ze which is necessary to suppress the further formation of Z-isomer product is dependent to some extent on conversion. At 70% conversion of 245fa, about 10-11% Z-isomer in the feed is required. At 80% conversion, about 13% Z-isomer in the feed is required In one embodiment, the reaction vessel can be held at a temperature of between 200° C. and 425° C. In another embodiment, the reaction vessel can be held at a temperature of between 250° C. and 350° C. In yet another embodiment, the reaction vessel can be held at a temperature of between 275° C. and 325° C. or between 350° C. to 410° C.

The reaction pressure can be subatmospheric, atmospheric, or superatmospheric. In one embodiment, the reaction is conducted at a pressure of from 14 psig to about 100 psig. In another embodiment, the reaction is conducted at a pressure of from 14 psig to about 60 psig. In yet another embodiment, the reaction is conducted at a pressure of from 40 psig to about 85 psig. In yet another embodiment, the reaction is conducted at a pressure of from 50 psig to 75 psig. In general, increasing the pressure in the reactor above atmospheric pressure will act to increase the contact time of the reactants in the process. Longer contact times will necessarily increase the degree of conversion in a process, without having to increase temperature.

Depending on the temperature of the reactor, and the contact time, the product mixture from the reactor will contain varying amounts of unreacted HFC-245fa. In certain embodiment, E-1,3,3,3-tetrafluoropropene, 1,1,3,3,3-pentafluoropropene, and HFO-1234yf may be separated from the Z-1,3,3,3-tetrafluoropropene, hydrogen fluoride, and any unreacted HFC-245fa, which are then recycled back to the reactor with additional HFC-245fa. Hydrogen fluoride may be removed by scrubbing, by passing the reactor effluent through a solution of aqueous caustic, or hydrogen fluoride may be removed by distillation. In particularly suitable embodiments, the composition formed from the process of the present disclosure includes both 1,3,3,3-tetrafluoropropene (HFO-1234ze(E)), HFO-1225zc and 2,3,3,3-tetrafluoropropene (HFO-1234yf), which are not separated.

In one embodiment, the reactor feed is preheated in a vaporizer to a temperature of from about 30° C. to about 100° C. In another embodiment, the reactor feed is preheated in a vaporizer to a temperature of from about 30° C. to about 80° C.

In some embodiments, an inert diluent gas is used as a carrier gas for the hydrochlorofluoropropane. In one embodiment, the carrier gas is selected from nitrogen, argon, helium, or carbon dioxide.

In one embodiment, the product mixture includes (on a mol basis) between 0.01% to 1.00% HFO-1234yf, alternatively between 0.05% to 0.95% HFO-1234yf, alternatively between 0.10% to 0.90% HFO-1234yf, alternatively between 0.20% to 0.80% HFO-1234yf, alternatively between 0.01% to 0.20% HFO-1234yf, alternatively between 0.10% to 0.30% HFO-1234yf, alternatively between 0.20% to 0.40% HFO-1234yf, alternatively between 0.30% to 0.50% HFO-1234yf, alternatively between 0.30% to 0.40% HFO-1234yf, alternatively between 0.40% to 0.60% HFC-1234yf, alternatively between 0.50% to 0.70% HFO-1234yf, alternatively between 0.60% to 0.80% HFO-1234yf, alternatively between 0.70% to 0.70% HFO-1234yf, alternatively between 0.80% to 1.00% HFO-1234yf. In another embodiment, the foregoing product mixtures further comprises (on a mole basis) HFO-1225zc wherein the HFO-1225zc is present in an amount equal to 10% of the HFO-1234yf.

In some embodiments, the fluoropropene composition additionally optionally comprises one or more of R-143a, R-152a, TFP, R-1233xf, R-1233zd(E), or R-1233zd(Z). In some embodiments, the sum total of the amounts of R-143a, R-152a, TFP, R-1233xf, R-1233zd(E), and R-1233zd(Z) is between 0.00001 mole percent and 2 mole percent, based on the total fluoropropene composition. In one embodiment, the fluoropropene composition includes R-1233zd(E) in an amount of 0.7 mole percent to 1.15 mole percent, based on the total heat transfer media. In one embodiment, the fluoropropene composition includes R-1233zd(Z) in an amount of 0.05 mole percent to 0.25 mole percent, based on the total heat transfer media. In one embodiment, the fluoropropene composition includes R-143a in an amount of 0.05 mole percent to 0.25 mole percent, based on the total fluoropropene composition.

In other embodiments, the fluoropropene composition optionally comprises one or more of 1224yd, 1224zc, 1326mxz, 113, 32, 23, trifluoro propyne, 356mff, 1326mxz, HFC-245fa and HFC-245cb. The amount of the foregoing compounds can range from about 0.001 to about 1 mole %, about 0.001 to about 0.9 and, in some cases, about 0.001 to about 0.7 mole %

In one particular embodiment, the sum total of the amounts 1224yd, 1224zc, 1326mxz, 113, 32, 23, trifluoro propyne, 356mff, 1326mxz, HFC-245fa and HFC-245cb is between 0.001 mole percent and 2 mole percent, based on the total fluoropropene composition. The amount of the foregoing compounds can range from about 0.001 to about 0.1 mole %, about 0.001 to about 0.09 and, in some cases, about 0.001 to about 0.07 mole %

In another particular embodiment, the inventive composition can comprise greater than about 99 wt % HFO-1234ze (E) and, for example, 99.5 to 99.99, 99.6 to 99.9 and in some cases about 99.7 to 99.99 wt % HFO-1234ze(E) with the remainder comprising HFO-1225zc and HFO-1234yf. The inventive compositions can also contain at least one additional compound selected from the group consisting of HFC-134a, 245cb, 236fa, 1225ye isomers (e.g., E-1225ye and Z-1225ye), HFO-1234ze isomer (e.g., HFO-1234ze(Z)), HFC-245fa, HFC-124, HCFC-114, trifluoropropyne, HFC-152a and HFO-1234 isomers including at least one member selected from the group consisting of HFO-1234zc, HFO-1234yc and HFO-1234ye. The total combined amount of HFO-1225zc, HFO-1234yf and the additional compound(s) can range from greater than 0 to less than about 1 wt. %, and for example, greater than 0 to 0.3, greater than 0 to 0.1 and in some cases greater than 0 to 0.01 mol %. A specific Example of the foregoing composition is shown in Table A below

TABLE A

| Components | |
|---|---|
| 134a | 3.2 ppm |
| 1225zc | 1.5 ppm |
| 1234yf | 47 ppm |
| 245cb | Coelute with yf |
| 236fa | 1.1 ppm |
| E-1234ze | 99.98 |
| E-1225ye | 0.6 ppm |
| 1234 isomers* | 6.1 ppm |
| 245fa | 20.5 ppm |
| 124 | 4.6 ppm |
| Z-1234ze | 87 ppm |
| 114 | 14 ppm |
| trifluoropropyne | 1 ppm |

TABLE A-continued

| Components | |
|---|---|
| 152a | 0.5 ppm |
| Z-1225ye | 4 ppm |

*Unknown includes HFO-1234zc, HFO-1234yc and HFO-1234ye

The fluoropropene composition may be useful in various applications. In an embodiment, the fluoropropene composition may be used as a refrigerant. In some embodiments, the fluoropropene composition may be used as a replacement for older generation refrigerants (e.g., R404A, R502) to provide a more environmentally friendly composition. In some embodiments, the fluoropropene composition may be a hydrofluoro-olefin composition. In an embodiment, the fluoropropene composition includes from 99 mole percent to 99.99 mole percent of 1,3,3,3-tetrafluoropropene (HFO-1234ze)(E) and from 0.0001 mole percent to 1.0 mole percent of 1,1,3,3,3-pentafluoropropene (HFO-1225zc) and 2,3,3,3-tetrafluoropropene (HFO-1234yf). In another embodiment, the fluoropropene composition is a near azeotropic composition that is substantially free of HFO-1234ze (Z). By substantially free, it is meant that the fluoropropene composition contains less than about 1000 ppm, less than about 500 ppm and typically less than about 100 ppm, HFO-1234ze(Z).

In one embodiment, the foregoing inventive fluoropropene compositions can be blended with other fluorochemicals. This embodiment of the present invention relates to a refrigerant composition comprising the inventive composition (e.g., HFO-1234ze(E), HFO-1225zc and HFO-1234yf) and at least one compound selected from the group consisting of: HFC-1234ye, HFC-1243zf, HFC-32, HFC-125, HFC-134, HFC-134a, HFC-143a, HFC-152a, HFC-161, HFC-227ea, HFC-236ea, HFC-236fa, HFC-245fa, HFC-365mfc, R1336mzz(E), propane, n-butane, isobutane, 2-methylbutane, n-pentane, cyclopentane, dimethylether, $CF_3SCF_3$, $CO_2$, $CF_3I$ and combinations thereof.

In one embodiment, the foregoing inventive fluoropropene compositions are combined with at least one additional refrigerant comprising a member selected from the group consisting of R32, R125, R134, R134a, 227ea, and R1336mzz(E). The amount of the at least one additional refrigerant can range from about 5 to about 95, about 50 to about 90 and in some cases about 60 to about 80 wt. % of the refrigerant composition. In one particular embodiment, the inventive fluoropropene compositions can be employed as a source of HFO-1234ze for preparing R444, R446A/B, R447B, R448A, R450A, R456, R459A/B, R460A/B/C, R464A, 515A and 515B.

In some embodiments, the foregoing fluoropropene compositions may be used in a refrigeration system. One embodiment of a refrigeration system includes an evaporator, a condenser, a compressor, an expansion device, and a heat transfer media. The heat transfer media includes the fluoropropene composition. The heat transfer media can further comprise at least one lubricant including those suitable for use with refrigeration or air-conditioning apparatus. Among these lubricants are those conventionally used in compression refrigeration apparatus utilizing chlorofluorocarbon refrigerants. Such lubricants and their properties are discussed in the 1990 ASHRAE Handbook, Refrigeration Systems and Applications, chapter 8, titled "Lubricants in Refrigeration Systems", pages 8.1 through 8.21, herein incorporated by reference. Lubricants of the present invention may comprise those commonly known as "mineral oils"

in the field of compression refrigeration lubrication. Mineral oils comprise paraffins (i.e. straight-chain and branched-carbon-chain, saturated hydrocarbons), naphthenes (i.e. cyclic or ring structure saturated hydrocarbons, which may be paraffins) and aromatics (i.e. unsaturated, cyclic hydrocarbons containing one or more rings characterized by alternating double bonds). Lubricants of the present invention further comprise those commonly known as "synthetic oils" in the field of compression refrigeration lubrication. Synthetic oils comprise alkylaryls (i.e. linear and branched alkyl alkylbenzenes), synthetic paraffins and naphthenes, silicones, and poly-alpha-olefins. Representative conventional lubricants of the present invention are the commercially available BVM 100 N (paraffinic mineral oil sold by BVA Oils), naphthenic mineral oil commercially available under the trademark from Suniso® 3GS and Suniso® 5GS by Crompton Co., naphthenic mineral oil commercially available from Pennzoil under the trademark Sontex® 372LT, naphthenic mineral oil commercially available from Calumet Lubricants under the trademark Calumet® RO-30, linear alkylbenzenes commercially available from Shrieve Chemicals under the trademarks Zerol® 75, Zerol® 150 and Zerol® 500 and branched alkylbenzene, sold by Nippon Oil as HAB 22.

In one embodiment, the lubricant component can comprise those which have been designed for use with refrigerants and are miscible with the fluoropropene compositions of the present invention under compression refrigeration and air-conditioning apparatus' operating conditions. Such lubricants and their properties are discussed in "Synthetic Lubricants and High-Performance Fluids", R. L. Shubkin, editor, Marcel Dekker, 1993. Such lubricants include, but are not limited to, polyol esters (POEs) such as Castrol® 100 (Castrol, United Kingdom), polyalkylene glycols (PAGs) such as RL-488A from Dow (Dow Chemical, Midland, Mich.), and polyvinyl ethers (PVEs).

Lubricants of the present invention are selected by considering a given compressor's requirements and the environment to which the lubricant will be exposed. The amount of lubricant can range from about 1 to about 50, about 1 to about 20 and in some cases about 1 to about 3 weight percent of a refrigerant composition. In one particular embodiment, the foregoing refrigerant compositions are combined with a PAG lubricant for usage in an automotive A/C system having an internal combustion engine. In another particular embodiment, the foregoing refrigerant compositions are combined with a POE lubricant for usage in an automotive A/C system having an electric or hybrid electric drive train.

In one embodiment, a refrigerant composition comprises the inventive near azeotropic composition, at least one lubricant and at least one additive which can improve the refrigerant and air-conditioning system lifetime and compressor durability are desirable. In one aspect of the invention, the foregoing refrigerant compositions comprise at least one member selected from the group consisting of acid scavengers, performance enhancers, and flame suppressants.

In another embodiment, the fluoropropene composition may be used in a process to transfer heat. The process may include providing an article and contacting the article with a heat transfer media including the fluoropropene composition. In some embodiments, the article may include electrical equipment (e.g., circuit board, computer, display, semiconductor chip, or transformer), a heat transfer surface (e.g., heat sink), or article of clothing (e.g., a body suit).

In another embodiment, the fluoropropene composition may be used in a process for treating a surface. The process may include providing a surface having a treatable material deposited thereon and contacting the surface with a treatment composition including the fluoropropene composition. In some embodiments, the treatment composition may substantially dissolve the treatable material.

In another embodiment, the fluoropropene composition may be used in a process for forming a composition. The process includes providing a solute and contacting the solute with a solvent including the fluoropropene composition. In some embodiments, the fluoropropene composition may substantially dissolve the solute.

In another embodiment, the present invention relates to blowing agent compositions comprising the fluoroolefin-containing compositions (e.g., near azeotropic containing compositions), as described herein for use in preparing foams. In other embodiments the invention provides foamable compositions, and preferably polyurethane and polyisocyanate foam compositions, and method of preparing foams. In such foam embodiments, one or more of the present fluoroolefin-containing compositions are included as a blowing agent in foamable compositions, which composition preferably includes one or more additional components capable of reacting and foaming under the proper conditions to form a foam or cellular structure. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention.

The present invention further relates to a method of forming a foam comprising: (a) adding to a foamable composition a fluoroolefin-containing composition of the present invention; and (b) reacting the foamable composition under conditions effective to form a foam.

Another embodiment of the present invention relates to the use of the fluoroolefin-containing compositions as described herein (e.g., near azeotropic compositions of HFO-1234ze(E), HFO-1225zc and HFO-1234yf), for use as propellants in sprayable compositions. Additionally, the present invention relates to a sprayable composition comprising the fluoroolefin-containing compositions as described herein. The active ingredient to be sprayed together with inert ingredients, solvents and other materials may also be present in a sprayable composition. Preferably, the sprayable composition is an aerosol. Suitable active materials to be sprayed include, without limitations, cosmetic materials, such as deodorants, perfumes, hair sprays, cleaners, and polishing agents as well as medicinal materials such as anti-asthma and anti-halitosis medications.

The present invention further relates to a process for producing aerosol products comprising the step of adding a fluoroolefin-containing composition as described herein to active ingredients in an aerosol container, wherein said composition functions as a propellant.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim, such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole. The transitional phrase "consisting essentially of" is used to define a composition, method that includes materials, steps, features, components, or elements, in addition to those literally disclosed provided that these additional included materials, steps, features, components, or elements do not materially affect the basic and novel characteristic(s) of the claimed invention, especially the mode of action to achieve the desired result of any of the processes of the present invention. The term 'consisting essentially of' occupies a middle ground between "comprising" and 'consisting of'.

In the foregoing combinations of inventive embodiments, the compositions can comprise, consist essentially of or consist of HFO-1234ze(E), HFO-1225zc and HFO-1234yf.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates the dehydrofluorination of 245fa over $Cr_2O_3$ in the presence of Z-HFC-1234ze.

An Inconel tube (½ inch OD) was filled with 10 cc (8 gm) of $Cr_2O_3$ catalyst (Johnson Mathey) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 1.

TABLE 1

| % Z-ze added | 0 | 7.5 | 10.9 |
|---|---|---|---|
| Incoming compos | 100/0 | 92.5/7.5 | 89/11 |
| 245fa conversion (%) | 71.2 | 69.3 | 72 |
| Z-ze in product (%) | 10.7 | 10.3 | 11.2 |
| % recovered 245fa | 28.8 | 28.4 | 24.9 |
| % E-ze | 60.5 | 60.3 | 63.9 |
| % yield E-ze | 60.5 | 65.3 | 71.7 |
| % selectivity E-ze | 85 | 94.2 | 99.7 |

Example 2

Example 2 demonstrates the dehydrofluorination of 245fa over $Cr_2O_3$ in the presence of Z-HFC-1234ze.

An Inconel tube (½ inch OD) was filled with 10 cc (8 gm) of $Cr_2O_3$ catalyst (Guignet's green) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 2.

TABLE 2

| % Z-ze added | 0 | 10.9 |
|---|---|---|
| Incoming compos | 100/0 | 89/11 |
| 245fa conversion (%) | 69.9 | 71.8 |
| Z-ze in product (%) | 10.7 | 10.9 |
| % recovered 245fa | 30.1 | 25.1 |
| % E-ze | 59.2 | 64 |
| % yield E-ze | 59.2 | 71.9 |
| % selectivity E-ze | 84.7 | 100 |

Example 3

Example 3 demonstrates the dehydrofluorination of 245fa over $Cr_2O_3$ in the presence of Z-HFC-1234ze.

An inconel tube (½ inch OD) was filled with 10 cc (8 gm) of $Cr_2O_3$ catalyst (Johnson Mathey) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued, and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 3.

TABLE 3

| % Z-ze added | 0 | 10.9 |
|---|---|---|
| Incoming compos | 100/0 | 89/11 |
| 245fa conversion (%) | 73 | 71.3 |
| Z-ze in product (%) | 11.4 | 11.0 |
| % recovered 245fa | 27.0 | 25.5 |
| % E-ze | 61.6 | 63.5 |
| % yield E-ze | 61.6 | 72.5 |
| % selectivity E-ze | 84 | 100 |

Example 4

Example 4 demonstrates the dehydrofluorination of 245fa over $Cr_2O_3$ in the presence of Z-HFC-1234ze.

An inconel tube (½ inch OD) was filled with 10 cc (8 gm) of $Cr_2O_3$ catalyst (Newport Cr) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 4.

TABLE 4

| % Z-ze added | 0 | 10.7 |
|---|---|---|
| Incoming compos | 100/0 | 89.3/10.7 |
| 245fa conversion (%) | 72.2 | 70.2 |
| Z-ze in product (%) | 10.4 | 10.5 |
| % recovered 245fa | 27.8 | 26.6 |
| % E-ze | 61.8 | 62.9 |
| % yield E-ze | 61.8 | 70.4 |
| % selectivity E-ze | 85.5 | 100 |

Example 5

Example 5 demonstrates the dehydrofluorination of 245fa over fluorided alumina in the presence of Z-HFC-1234ze.

An inconel tube (½ inch OD) is filled with 10 cc (6.1 gm) of $Al_2O_3$ catalyst (purchased from Sigma-Aldrich). $Al_2O_3$ in extrudate form, which is crushed and sieved to 12/20 mesh. After charging the reactor tube, the temperature of the catalyst bed is raised to 300° C. and purged with nitrogen (30 cc/min) for 200 minutes. Then the flow of nitrogen is reduced to 60 cc/min and HF is fed at 20 cc/min for 60 minutes. The temperature is increase to 325° C. for 300 minutes. The flow of nitrogen is then lowered to 30 cc/min and the flow of HF is raised to 30 cc/min for 30 minutes. The flow of nitrogen is then lowered to 12 cc/min and the flow of HF is raised to 48 cc/min for 60 minutes. The flow of nitrogen is then discontinued, and the flow of HF is raised to 48 cc/min for 30 minutes. The reactor temperature is then decreased to 250° C. for 30 minutes. Afterwards HF is turned off and the reactor is purged with 30 cc/min of nitrogen. The reactor temperature is then stabilized at 300° C., the flow of nitrogen is turned off, and either $CF_3CH_2CHF_2$, or $CF_3CH_2CHF_2$ with varying amounts of Z-1234ze, is fed at 1.44 ml/hr. Contact time in the reactor is 45 seconds.

The $CF_3CH_2CHF_2$ is vaporized at 50° C. Part of the reactor effluent is passed through a series of valves and analyzed by GCMS. Amounts for Z-1234ze, 245fa and E-1234ze are expressed as mole percent. Results are summarized in Table 5.

TABLE 5

| % Z-ze added | 0 | 10.9 |
|---|---|---|
| Incoming compos | 100/0 | 89/11 |
| 245fa conversion (%) | 70 | 71 |
| Z-ze in product (%) | 11 | 11 |
| % recovered 245fa | 30 | 29 |
| % E-ze | 59 | 58 |
| % yield E-ze | 59 | 65 |
| % selectivity E-ze | 84.3 | 100 |

Example 6

Table 6 discloses the reaction products of the dehydrofluorination of 245fa over various catalysts in the presence of Z-HFC-1234ze (in mol %).

TABLE 6

| Catalyst | Unknown | 143a | 152a | TFP | 1234yf | 1233xf |
|---|---|---|---|---|---|---|
| JM 62-2 | 0.15% | 0.13% | 0.00% | 0.01% | 0.35% | 0.03% |
| LV | 0.28% | 0.14% | 0.03% | 0.02% | 0.04% | 0.00% |
| JM-62-3 | 0.28% | 0.14% | 0.02% | 0.02% | 0.24% | 0.04% |
| Newport-Chrome | 0.12% | 0.13% | 0.00% | 0.00% | 0.92% | 0.00% |

| Catalyst | E-1233zd | Z-1233zd | Z-1234ze | E-1234ze | E + Z-1234ze |
|---|---|---|---|---|---|
| JM 62-2 | 0.88% | 0.13% | 11.17% | 87.13% | 98.3% |
| LV | 1.03% | 0.15% | 10.9% | 87.4% | 98.3% |
| JM-62-3 | 0.92% | 0.14% | 11% | 87.2% | 98.2% |
| Newport-Chrome | 0.92% | 0.11% | 10.5% | 87.3% | 97.8% |

An inconel tube (½ inch OD) was filled with 10 cc (8 gm) of catalyst (see Table 6). After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued, and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with 10.5-11% of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 134a, 152b, TFP, 1234yf, 1233xf, E-1233zd, Z-1233zd and E+Z-1234ze are expressed as mole percent. Results are summarized in Table 6. A grab sample was also taken for off-line GCMS analysis. It was detected that the Unknowns of Table 6 (some of them coelute with other peaks) contained 236fa, 1225zc, 1225ye (E and Z), 1234ye, 1234zc and trifluoropropyne.

While any GCMS equipment, method and parameters, which are suitable for detecting the compounds that may be present in the inventive compositions, can be employed, one suitable method uses a single RTX-1 column.

Example 7

Table 7 shows the near azeotropic characteristic of various compositions, which can be produced by the method of the present invention, by measuring Delta P of vapor pressure in terms of percent change. Delta P vapor pressure is the vapor pressure change at −25° C. after a 50% vapor leak wherein 50% of the vapor is removed.

TABLE 7

| 1234zeE/1234yf wt % | Delta P % |
|---|---|
| 99/1 | 0.45 |
| 99.1/0.9 | 0.40 |
| 99.2/0.8 | 0.36 |
| 99.3/0.7 | 0.31 |
| 99.4/0.6 | 0.28 |
| 99.5/0.5 | 0.22 |
| 99.6/0.4 | 0.19 |

TABLE 7-continued

| 1234zeE/1234yf wt % | Delta P % |
|---|---|
| 99.7/0.3 | 0.13 |
| 99.8/0.2 | 0.09 |
| 99.9/0.1 | 0.04 |
| 99.91/0.09 | 0.04 |
| 99.95/0.05 | 0.03 |
| 99.96/0.04 | 0.02 |
| 99.97/0.03 | 0.01 |
| 99.98/0.02 | 0.009 |
| 99.99/0.01 | 0.005 |
| 99.9987/.0013 | 0.001 |

Example 8

Table 8 shows the cooling performance of various near azeotropic compositions, which can be produced by the method of the present invention, by comparing cooling capacity and energy efficiency (COP) to HFO-1234ze(E). The data are based on the following conditions.
T_condenser=47.0 deg C
T_evaporator=7.0 deg C
subcool=12.0 K
superheat=3.0 K
compressor efficiency=0.7
Average Heat Exchanger Temperature Set Points
Superheat is included in refrigeration effect
cooling load=1.0 tonnes
compressor displacement=0.1 (m^3/min)

TABLE 8

| | Mol % | Cooling Capacity (kJ/m3) | Capacity Rel to 1234ze (%) | COP | COP Rel to 1234ze (%) |
|---|---|---|---|---|---|
| 1234ze | 100 | 2111 | 100.0% | 4.402 | 100.0% |
| 1234ze/1234yf | 99.9/0.1 | 2112 | 100.0% | 4.402 | 100.0% |
| 1234ze/1234yf | 99.7/0.3 | 2114 | 100.1% | 4.402 | 100.0% |
| 1234ze/1234yf | 99.5/0.5 | 2116 | 100.2% | 4.402 | 100.0% |
| 1234ze/1234yf | 99.1/0.9 | 2120 | 100.4% | 4.401 | 100.0% |

Example 8 illustrates that the inventive near azeotropic compositions are effective for use as refrigerants and have refrigeration properties at least equivalent to HFO-1234ze (E).

Example 9

An inconel tube (½ inch {13 mm} OD) was filled with 5 cc (3.9 gm) of $Cr_2O_3$ catalyst (Louisville Cr) which was activated as described in Example 6. After activation, the flow of nitrogen was turned off, and the reactor temperature was set to 400° C. A flow of air (4 vol % O2) and either $CF_3CH_2CHF_2$ (245fa alone), or $CF_3CH_2CHF_2$ with 13.3 mole % (corresponding to 11.5 wt %) of Z-1234ze, was fed at 0.67 ml/hr. Contact time in the reactor was 38 seconds. The $CF_3CH_2CHF_2$ was vaporized at 50° C. Part of the reactor effluent was passed through a series of valves and analyzed by GCMS. After 72 hours the flow of oxygen was stopped and the reactions were continued for another 72 hours in the absence of an oxygen containing gas. The catalysts started deactivating at a total time of about 120 hours for the reaction run with 245fa alone and at a total time of about 136 hours for the reaction run with 245fa containing Z-1234ze. Results are summarized in the following table with the amounts for Z-1234ze, 245fa and E-1234ze being expressed as mole percent:

TABLE 9

| % Z-ze added | 0 | 0 | 13.3 | 13.3 |
|---|---|---|---|---|
| oxygen | yes | no | yes | no |
| Incoming composition | 100/0 | 100/0 | 86.7/13.3 | 86.7/13.3 |
| 245fa conversion (%) | 96.1 | 89.7 | 95.8 | 89.5 |
| Z-ze in product (%) | 22.9 | 21.1 | 22.7 | 20.8 |
| % recovered 245fa | 3.9 | 10.4 | 3.8 | 9.3 |
| % E-ze | 73.2 | 68.6 | 73.5 | 69.9 |
| % yield E-ze | 73.2 | 60.2 | 85.0 | 80.9 |
| % selectivity E-ze | 76.2 | 76.4 | 88.7 | 90.2 |

Example 10

Table 10 shows the cooling performance of various refrigerant compositions comprising HFO-1234ze(E), HFO-1225zc and HFO-1234yf, which can be produced by the method of the present invention, by comparing cooling capacity and energy efficiency (COP) to HFO-1234ze(E). The data are based on the following conditions

TABLE 10

ThermPy Results

| fluid | CAP_c (kJ/m^3) | COP_c | delta P % - 50% mass leak at −25° C. |
|---|---|---|---|
| R-1234zeE | 2111.4 | 4.402 | 0.000 |
| _R-1234yf_R-1225zc_R-1234zeE_W = _0.0_0.005_0.995 | 2112.4 | 4.402 | −0.023 |
| _R-1234yf_R-1225zc_R-1234zeE_W = _0.00125_0.00375_0.995 | 2113.3 | 4.402 | −0.089 |
| _R-1234yf_R-1225zc_R-1234zeE_W = _0.0025_0.0025_0.995 | 2114.2 | 4.402 | −0.158 |
| _R-1234yf_R-1225zc_R-1234zeE_W = _0.00375_0.00125_0.995 | 2115.2 | 4.402 | −0.220 |
| _R-1234yf_R-1225zc_R-1234zeE_W = _0.005_0.0_0.995 | 2116.1 | 4.402 | −0.285 |
| R-515B | 2100.4 | 4.393 | −0.001 |
| _R-1225zc_R-1234yf_R-1234zeE_R-227ea_W = _0.0_0.00456_0.90644_0.089 | 2104.6 | 4.392 | −0.255 |
| _R-1225zc_R-1234yf_R-1234zeE_R-227ea_W = _0.00114_0.00342_0.90644_0.089 | 2103.7 | 4.392 | −0.197 |
| _R-1225zc_R-1234yf_R-1234zeE_R-227ea_W = _0.00228_0.00228_0.90644_0.089 | 2102.9 | 4.392 | −0.139 |
| _R-1225zc_R-1234yf_R-1234zeE_R-227ea_W = _0.00342_0.00114_0.90644_0.089 | 2102.1 | 4.392 | −0.080 |
| _R-1225zc_R-1234yf_R-1234zeE_R-227ea_W = _0.00456_0.0_0.90644_0.089 | 2101.3 | 4.393 | −0.021 |
| R-515A | 2096.1 | 4.389 | −0.003 |
| _R-1225zc_R-1234yf_R-1234zeE_R-227ea_W = _0.0_0.0044_0.8756_0.12 | 2100.1 | 4.389 | −0.245 |
| _R-1225zc_R-1234yf_R-1234zeE_R-227ea_W = _0.0011_0.0033_0.8756_0.12 | 2099.3 | 4.389 | −0.190 |
| _R-1225zc_R-1234yf_R-1234zeE_R-227ea_W = _0.0022_0.0022_0.8756_0.12 | 2098.5 | 4.389 | −0.134 |
| _R-1225zc_R-1234yf_R-1234zeE_R-227ea_W = _0.0033_0.0011_0.8756_0.12 | 2097.7 | 4.389 | −0.078 |
| _R-1225zc_R-1234yf_R-1234zeE_R-227ea_W = _0.0044_0.0_0.8756_0.12 | 2096.9 | 4.389 | −0.022 |
| R-450A | 2465.1 | 4.394 | −1.86 |
| _R-1225zc_R-1234yf_R-1234zeE_R-134a_W = _0.0_0.0029_0.5771_0.42 | 2467.7 | 4.394 | −1.92 |
| _R-1225zc_R-1234yf_R-1234zeE_R-134a_W = _0.00073_0.00218_0.5771_0.42 | 2467.2 | 4.394 | −1.90 |
| _R-1225zc_R-1234yf_R-1234zeE_R-134a_W = _0.00145_0.00145_0.5771_0.42 | 2466.8 | 4.394 | −1.89 |
| _R-1225zc_R-1234yf_R-1234zeE_R-134a_W = _0.00218_0.00073_0.5771_0.42 | 2466.3 | 4.394 | −1.87 |
| _R-1225zc_R-1234yf_R-1234zeE_R-134a_W = _0.0029_0.0_0.5771_0.42 | 2465.9 | 4.394 | −1.86 |
| Refrigerant A | 2276.7 | 4.421 | −0.084 |
| _R-1225zc_R-1234yf_R-1234zeE_R-134_W = _0.0_0.00315_0.62685_0.37 | 2279.3 | 4.421 | −0.199 |

TABLE 10-continued

ThermPy Results

| fluid | CAP_c (kJ/m^3) | COP_c | delta P % - 50% mass leak at −25° C. |
|---|---|---|---|
| _R-1225zc_R-1234yf_R-1234zeE_R-134_W = _0.00079_0.00236_0.62685_0.37 | 2278.9 | 4.421 | −0.175 |
| _R-1225zc_R-1234yf_R-1234zeE_R-134_W = _0.00157_0.00157_0.62685_0.37 | 2278.5 | 4.421 | −0.151 |
| _R-1225zc_R-1234yf_R-1234zeE_R-134_W = _0.00236_0.00079_0.62685_0.37 | 2278.1 | 4.421 | −0.127 |
| _R-1225zc_R-1234yf_R-1234zeE_R-134_W = _0.00315_0.0_0.62685_0.37 | 2277.7 | 4.421 | −0.103 |
| Refrigerant B | 1885.4 | 4.409 | −5.82 |
| _R-1225zc_R-1234yf_R-1234zeE_R-1336mzzE_R-227ea_W = _0.0_0.00393_0.78307_0.17_0.043 | 1888.8 | 4.408 | −6.10 |
| _R-1225zc_R-1234yf_R-1234zeE_R-1336mzzE_R-227ea_W = _0.00098_0.00295_0.78307_0.17_0.043 | 1888.1 | 4.408 | −6.04 |
| _R-1225zc_R-1234yf_R-1234zeE_R-1336mzzE_R-227ea_W = _0.00197_0.00197_0.78307_0.17_0.043 | 1887.4 | 4.408 | −5.98 |
| _R-1225zc_R-1234yf_R-1234zeE_R-1336mzzE_R-227ea_W = _0.00295_0.00098_0.78307_0.17_0.043 | 1886.7 | 4.408 | −5.91 |
| _R-1225zc_R-1234yf_R-1234zeE_R-1336mzzE_R-227ea_W = _0.00393_0.0_0.78307_0.17_0.043 | 1886.1 | 4.408 | −5.85 |
| R-448A | 4718.7 | 4.214 | −14.4 |
| _R-1225zc_R-1234yf_R-1234zeE_R-125_R-134a_R-32_W = _0.0_0.20035_0.06965_0.26_0.21_0.26 | 4719 | 4.214 | −14.3 |
| _R-1225zc_R-1234yf_R-1234zeE_R-125_R-134a_R-32_W = _9e-05_0.20026_0.06965_0.26_0.21_0.26 | 4719 | 4.214 | −14.3 |
| _R-1225zc_R-1234yf_R-1234zeE_R-125_R-134a_R-32_W = _0.00017_0.20017_0.06965_0.26_0.21_0.26 | 4719 | 4.214 | −14.3 |
| _R-1225zc_R-1234yf_R-1234zeE_R-125_R-134a_R-32_W = _0.00026_0.20009_0.06965_0.26_0.21_0.26 | 4719 | 4.214 | −14.4 |
| _R-1225zc_R-1234yf_R-1234zeE_R-125_R-134a_R-32_W = _0.00035_0.2_0.06965_0.26_0.21_0.26 | 4718.9 | 4.214 | −14.4 |

T_condenser = 47.0° C.
T_evaporator = 7.0° C.
subcool = 12.0 K
superheat = 3.0 K
compressor efficiency = 0.7
Average Heat Exchanger Temperature Set Points
Superheat is included in refrigeration effect.
cooling load = 3.517 kW
compressor displacement = 0.00283168438736 (m^3/min)

Note that not all the activities described above in the general description or the examples are required, that a portion of a specific activity may not be required, and that one or more further activities may be performed in addition to those described. Still further, the order in which activities are listed are not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A refrigerant composition comprising Z-1,3,3,3-tetrafluoropropene, E-1,3,3,3,-tetrafluoropropene, 1,1,3,3,3-pentafluoropropene, 2,3,3,3-tetrafluoropropene and at least one member selected from the groups consisting of:
   (a) R-143a, R-152a, TFP, R-1233xf, R-1233zd(E), R-1233zd(Z) 1224yd, 1224zc, 1326mxz, 113, 32, 23, trifluoropropyne, 1326mxz, HFC-245cb 1234zc, 1234yc, 1234ye, 134a, 1225ye (Z and E), 114, 124, and 236fa,
   (b) R-143a, R-152a, TFP, R-1233xf, R-1233zd(E), R-1233zd(Z), 1224yd, 1224zc, 1326mxz, 113, 32, 23, trifluoropropyne, 1326mxz, and HFC-245cb, and
   (c) HFC-1234ye, HFC-1243zf, HFC-32, HFC-125, HFC-134, HFC-134a, HFC-143a, HFC-152a, HFC-161, HFC-227ea, HFC-236ea, HFC-236fa, R1336mzz(E), propane, n-butane, isobutane, 2-methylbutane, n-pentane, cyclopentane, dimethylether, CF3SCF3, CO2, and CF3I; and wherein the refrigerant composition comprises greater than about 99 wt. % E-1,3,3,3-tetrafluoropropene and less than about 1,000 ppm of Z-1,3,3,3-tetrafluoropropene.

2. The refrigerant of claim 1 wherein 2,3,3,3-tetrafluoropropene and 1,1,3,3,3-pentafluoropropene both being present and wherein the total amount of 1,1,3,3,3-pentafluoropropene and 2,3,3,3-tetrafluoropropene is less than 1.0 mol %.

3. The refrigerant of claim 1 wherein the 2,3,3,3-tetrafluoropropene is present in an amount of 0.1 to 0.9 mol %.

4. The refrigerant of claim 1 wherein the 2,3,3,3-tetrafluoropropene is present in an amount of 0.2 to 0.4 mol %.

5. The refrigerant of claim 1 wherein the 2,3,3,3-tetrafluoropropene is present in an amount of 0.3 to 0.4 mol %.

6. The refrigerant of claim 1 wherein the member comprises one or more of R-143a, R-152a, TFP, R-1233xf, R-1233zd(E), R-1233zd(Z) 1224yd, 1224zc, 1326mxz, 113, 32, 23, trifluoro propyne, 356mff, 1326mxz, HFC-245cb 1234zc, 1234yc, 1234ye, 134a, 1225ye (Z and E), 114, 124, and 236fa.

7. The refrigerant of claim 6 wherein the sum total of the amounts of R-143a, R-152a, TFP, R-1233xf, R-1233zd(E), R-1233zd(Z), 1224yd, 1224zc, 1326mxz, 113, 32, 23, trifluoro propyne, 356mff, 1326mxz, and HFC-245cb is between 0.001 mole percent and 2 mole percent, based on the total fluoropropene composition.

8. The refrigerant of claim 1 wherein the refrigerant includes R-1233zd(E) in an amount of 0.7 mole percent to 1.15 mole percent, based on the total fluoropropene composition.

9. The refrigerant of claim 1 wherein the refrigerant includes R-1233zd(Z) in an amount of 0.05 mole percent to 0.25 mole percent, based on the total fluoropropene composition.

10. The refrigerant of claim 1 wherein the refrigerant includes R-143a in an amount of 0.05 mole percent to 0.25 mole percent, based on the total fluoropropene composition.

11. The refrigerant of claim 1 wherein the refrigerant is near azeotropic.

12. The refrigerant of claim 1 wherein the member comprises at least one member selected from the group consisting of HFC-1234ye, HFC-1243zf, HFC-32, HFC-125, HFC-134, HFC-134a, HFC-143a, HFC-152a, HFC-161, HFC-227ea, HFC-236ea, HFC-236fa, HFC 365mfc, R1336mmz(E), propane, n-butane, isobutane, 2-methylbutane, n-pentane, cyclopentane, dimethylether, CF3SCF3, CO2, and CF3I.

13. A process for transferring heat, comprising:
providing an article;
contacting the article with a heat transfer media;
wherein the heat transfer media comprises the composition of claim 1.

14. A refrigeration system, comprising:
an evaporator; a condenser;
a compressor;
an expansion device; and a heat transfer media;
wherein the heat transfer media comprises the composition of claim 1.

15. The refrigerant of claim 1 wherein the member comprises one or more of R-143a, R-152a, TFP, R-1233xf, R-1233zd(E), R-1233zd(Z), 1224yd, 1224zc, 1326mxz, 113, 32, 23, trifluoropropyne, 1326mxz and HFC-245cb.

16. The refrigerant of claim 1 further comprising at least one lubricant.

17. The refrigerant of claim 1 wherein the member comprises of at least one of R-143a, R-152a, R-1233xf, R-1233zd(E), 1224yd, trifluoropropyne, HFC-245cb 1234zc, 134a, 1225ye (Z and E), 114, 124, and 236fa.

18. The refrigerant of claim 1 wherein the member comprises at least one of R-143a, R-152a, TFP, R-1233xf, R-1233zd(E), 1224yd, 32, trifluoropropyne, and HFC-245cb.

19. The refrigerant of claim 1 wherein the member comprises at least one of HFC-1243zf, HFC-32, HFC-125, HFC-134, HFC-134a, HFC-143a, HFC-152a, HFC-227ea, HFC-236fa, R1336mzz(E), propane, n-butane, isobutane, 2-methylbutane, n-pentane, cyclopentane, dimethylether, and $CO_2$.

20. The refrigerant of claim 1 further comprising HFC-245fa.

* * * * *